US010172839B2

(12) United States Patent
Longo et al.

(10) Patent No.: US 10,172,839 B2
(45) Date of Patent: Jan. 8, 2019

(54) USE OF SHORT TERM STARVATION REGIMEN IN COMBINATION WITH KINASE INHIBITORS TO ENHANCE TRADITIONAL CHEMO-DRUG EFFICACY AND FEASIBILITY AND REVERSE SIDE EFFECTS OF KINASES IN NORMAL CELLS AND TISSUES

(71) Applicant: UNIVERSITY OF SOUTHERN CALIFORNIA, Los Angeles, CA (US)

(72) Inventors: Valter D. Longo, Playa del Rey, CA (US); Stefano Di Biase, Redondo Beach, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 14/671,622

(22) Filed: Mar. 27, 2015

(65) Prior Publication Data
US 2015/0250771 A1 Sep. 10, 2015

Related U.S. Application Data

(63) Continuation of application No. PCT/US2015/019102, filed on Mar. 6, 2015.

(60) Provisional application No. 61/948,792, filed on Mar. 6, 2014.

(51) Int. Cl.
*A01N 61/00* (2006.01)
*A61K 31/00* (2006.01)
*A61K 38/00* (2006.01)
*A61K 9/00* (2006.01)
*A61K 47/18* (2017.01)
*A61K 31/436* (2006.01)
*A61K 31/704* (2006.01)
*A61K 31/4745* (2006.01)
*A61K 31/475* (2006.01)

(52) U.S. Cl.
CPC .......... *A61K 31/436* (2013.01); *A61K 31/475* (2013.01); *A61K 31/4745* (2013.01); *A61K 31/704* (2013.01)

(58) Field of Classification Search
None
See application file for complete search history.

(56) References Cited

U.S. PATENT DOCUMENTS

| 6,670,392 | B2 | 12/2003 | Fleshner |
| 8,211,700 | B2 | 7/2012 | Longo |
| 8,728,815 | B2 | 5/2014 | Longo |
| 8,865,646 | B2 | 10/2014 | Longo |
| 9,237,761 | B2 | 1/2016 | Longo et al. |
| 9,386,790 | B2 | 7/2016 | Longo et al. |
| 9,522,910 | B2 | 12/2016 | Chilov et al. |
| 2008/0166427 | A1 | 7/2008 | Nomura et al. |
| 2008/0242638 | A1* | 10/2008 | Longo ................ G01N 33/5011 514/90 |
| 2011/0118528 | A1 | 5/2011 | Longo et al. |
| 2013/0045215 | A1 | 2/2013 | Longo et al. |
| 2013/0316948 | A1 | 11/2013 | Longo et al. |
| 2014/0112909 | A1 | 4/2014 | Longo et al. |
| 2014/0227373 | A1 | 8/2014 | Longo et al. |
| 2014/0328863 | A1 | 11/2014 | Longo |
| 2015/0133370 | A1 | 5/2015 | Longo |
| 2016/0331016 | A1 | 11/2016 | Longo et al. |
| 2017/0000183 | A1 | 1/2017 | Longo et al. |

FOREIGN PATENT DOCUMENTS

| EP | 2 719 696 A1 | 4/2014 |
| RU | 2346685 C2 | 9/2009 |
| WO | 2011/050302 A2 | 4/2011 |
| WO | 2012169934 A1 | 12/2012 |
| WO | 2012173521 A1 | 12/2012 |

OTHER PUBLICATIONS

CANSA, Cancer Association of South Africa, CANSA Detectives, Novel Strategies in Chemotherapeutic Intervention, Nov. 2013.*
U.S. Appl. No. 15/297,672, filed Oct. 19, 2016, inventors: Valter D. Longo et al.; Applicant: University of Southern California, title: "Methods and Formulations Promoting Tissue/Organ Regeneration, Longevity and Healthspan", 85 pgs.
Lee, C., et al., "Fasting Cycles Retard Growth of Tumors and Sensitize a Range of Cancer Cell Types to Chemotherapy," www.ScienceTranslationalMedicine.org, V. 4,Issues 124-127, Mar. 2012 compilation, pp. 74-83.
Liu, M. et al, "Antitumor Activity of Rapamycin in a Transgenic Mouse Model of ErbB2-Dependent Human Breast Cancer," Cancer Res., 2005, 65:(12), pp. 5325-5326.
Misawa, A., et al., "Rapamycin Inhibits Proliferation of Human Neuroblastoma Cells Without Suppression of MycN," Int. J. Cancer, 104, 2003, pp. 233-237.
Safdie, F.M. et al, "Fasting and Cancer Treatment in Humans: A Case Series Report," Aging, 2009, v. 1, n. 12, pp. 1-20.
Safdie, F. et al, "Fasting Enhances the Response of Glioma to Chemo- and Radiotherapy," PLOS ONE, 2012, v. 7, Issue 9, pp. 1-9.
Supplemental European Search Report dated Oct. 18, 2017 for EP Appn. No. 15759326.0 filed Sep. 15, 2016, 10 pgs.
Laviano, A. et al., "Toxicity in chemotherapy-when less is more," The New England Journal of Medicine, v. 366, n. 24, 2012, pp. 2319-2320.
English Translation of Russian Office Action dated Oct. 11, 2018, Russian Appn. No. 2016136638, 6 pgs.
English Translation of Search Report dated Oct. 10, 2018, Russian Appn. No. 2016136638, 2 pgs.

* cited by examiner

*Primary Examiner* — Layla D Berry
(74) *Attorney, Agent, or Firm* — Brooks Kushman P.C.

(57) ABSTRACT

A method of alleviating or treating symptoms of cancer and/or effects of chemotherapy or of kinase inhibitors includes a step of identifying a subject having cancer. A reduced caloric diet is administered to the subject for a first time period, the reduced caloric diet providing at most 1000 kcal per day. A kinase inhibitor is administered to the subject.

23 Claims, 9 Drawing Sheets

USE OF SHORT TERM STARVATION REGIMEN IN COMBINATION WITH KINASE INHIBITORS TO ENHANCE TRADITIONAL CHEMO-DRUG EFFICACY AND FEASIBILITY AND REVERSE SIDE EFFECTS OF KINASES IN NORMAL CELLS AND TISSUES

CROSS-REFERENCE TO RELATED APPLICATION

This application is the continuation of PCT Application No. PCT/US2015/019102 filed Mar. 6, 2015 which claims the benefit of U.S. provisional application Ser. No. 61/948,792 filed Mar. 6, 2014, the disclosures of which are incorporated in their entirety by reference herein.

STATEMENT REGARDING FEDERALLY SPONSORED RESEARCH OR DEVELOPMENT

The invention was made with Government support under Contract No. 1PO1AG034906 awarded by the National Institutes of Health. The Government has certain rights to the invention.

TECHNICAL FIELD

In at least one aspect, the present invention relates to methods to specifically target and kill cancer cells and alleviate toxic effects of chemotherapy.

BACKGROUND

Cancer is a ubiquitous disease afflicting mammals and in particular humans. Progress in treating cancer has been steady though a non-surgical cure in most cancers has not been realized. Research has shown that cancer is a multi-faceted illness that is currently not completely understood. Therefore, future treatment protocols will undoubtedly involve pathways not currently appreciated.

A relatively new pathway for treating cancer involves Short-Term Starvation (STS) and Fasting Mimicking Diets. Short-term starvation and fasting mimicking diets have been shown to be effective in the sensitization of a variety of cancer cell types to chemotherapy by Differential Stress Sensitization (DSS), while protecting normal cells and tissues by Differential Stress Resistance (DSR).

Accordingly, there is a need for improved methods for treating subject afflicted with cancer.

SUMMARY

The present invention solves one or more problems of the prior art by providing, in at least one embodiment, a method of alleviating or treating symptoms of cancer and/or effects of chemotherapy or of kinase inhibitors. The method includes a step of identifying a subject having cancer. A reduced caloric diet is administered to the subject for a first time period. Characteristically, the reduced caloric diet provides at most 1000 kcal per day. A kinase inhibitor is administered to the subject.

In another embodiment, a method for treating cancer and/or alleviating a symptom of chemotherapy is provided. The method includes a step of identifying a subject having cancer. A reduced caloric diet is administered to the subject for a first time period. Characteristically, the reduced caloric diet provides at most 1000 kcal per day. A chemotherapeutic agent is administered to the subject after the first time period.

In another embodiment, a method for alleviating a side effect of kinase inhibitor treatment is provided. The method includes a step of identifying a subject being treated with a kinase inhibitor. A reduced caloric diet is administered to the subject for a first time period. Characteristically, the reduced caloric diet provides at most 1000 kcal per day. A kinase inhibitor is administered to the subject.

Advantageously in the embodiments of the invention, STS or FMD in combination with kinases inhibitors is used to: a) offer a safe and powerful tool in the treatment of cancer without chemotherapy, b) potentiate the already beneficial effect of short term starvation in combination with chemo-drugs in cancer treatment (FIGS. 3 and 4), and c) to reverse the toxic effects observed during administration of the kinase inhibitors combined with traditional chemo-drugs alone (FIG. 2).

DETAILED DESCRIPTION

Figure 1A:
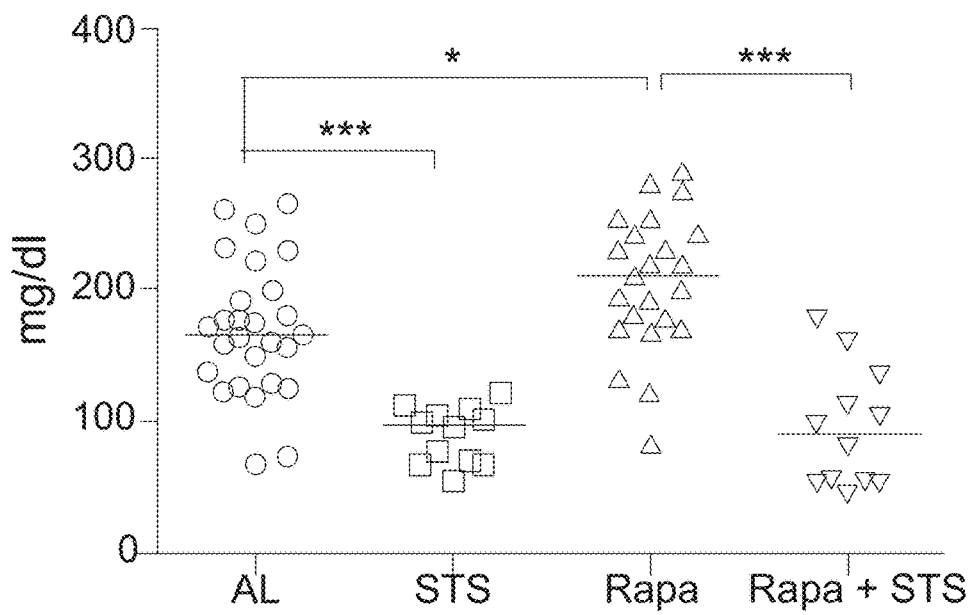
FIG. 1A provides plots of blood glucose levels for mice treated with STS, Rapamycin, and rapamycin with STS.

Reference will now be made in detail to presently preferred compositions, embodiments and methods of the present invention. The Figures are not necessarily to scale. The disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

This invention is not limited to the specific embodiments and methods described below, as specific components and/or conditions may, of course, vary. Furthermore, the terminology used herein is used only for the purpose of describing particular embodiments of the present invention and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The term "essential amino acid" refers to amino acids that cannot be synthesized by an organism. In humans, essential amino acids include isoleucine, leucine, lysine, methionine, phenylalanine, threonine, tryptophan, valine. In addition, the following amino acids are also essential in humans under certain conditions—histidine, tyrosine, and selenocysteine.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

Abbreviations:
"AL" mean ad lib.
"DSS" means differential stress sensitization.
"DXR" means doxorubicin.
"FMD" means fasting mimicking diet.
"KB" means ketone bodies.
"mTOR" means the mammalian target of rapamycin.
"PKA" mean protein kinase A.
"Rapa" means rapamycin.
"STS" means short-term starvation.
"TVD" means topotecan+vincristine+doxorubicin.

In an embodiment, a method of alleviating or treating symptoms of cancer and/or side effects of chemotherapy or side effects of kinase inhibitors includes a step of identifying a subject in need thereof. A reduced caloric diet is administered to the subject for a first time period. Characteristically, the reduced caloric diet providing at most 1000 kcal per day. A kinase inhibitor is administered to the subject before, after, or during the first time period.

In another embodiment, a method for alleviating a side effect of kinase inhibitor treatment is provided. The method includes a step of identifying a subject being treated with a kinase inhibitor. In a refinement, the kinase inhibitor is an mTOR protein kinase. A reduced caloric diet is administered to the subject for a first time period. Characteristically, the reduced caloric diet provides at most 1000 kcal per day. A kinase inhibitor is administered to the subject. In some refinements, the steps of administering the reduced caloric diet and administering of the kinase inhibitor constitute a treatment cycle that can be repeated a plurality of times as set forth below.

In still another embodiment of the present invention, a subject having cancer and/or receiving chemotherapy is identified. A kinase inhibitor (e.g., Rapamyicin) is administered to the subject along with a reduced caloric diet. The reduced caloric diet is either a short-term starvation (STS) or a fasting mimicking diet (FMD) that is administered for a first time period. In a refinement, the kinase inhibitor is an mTOR protein kinase. In short-term starvation, the subject is provided with substantially 0 kilocalories per day. In general, the FMD diet provides less than about 1000 kilocalories per day when administered. Details of the FMD diet are set for the below in more detail. In another variation, a chemotherapeutic agent that is different than the kinase inhibitor is also administered to the subject during treatment. Examples of suitable chemotherapeutic agents include, but are not limited to, topotecan, vincristine, doxorubicin, and combinations thereof. Dosages of the chemotherapeutic agents are those known in the art for treating various cancers with such agents. The present embodiment is found particularly useful for treating subject having melanoma, neuroblastoma, or breast cancer or being treated by chemotherapy for these conditions. Moreover, the treatment protocol of the present embodiment results in a lower tumor volume than treatment with chemotherapeutic agents that do not combine kinase inhibitors with the reduced caloric diet set forth herein. In other refinements, the steps of administering the reduced caloric diet, administering of the chemotherapeutic agent and administering of the kinase inhibitor constitute a treatment cycle that can be repeated a plurality of times. Advantageously, the methods of the invention which include STS or FMDs. reduce or completely reverse mortality induced by doxorubicin and worsened by the combination of doxorubicin and rapamycin.

In the context of the present embodiments, it should be appreciated that multiple changes occur during STS and FMD at the molecular and physiological levels including (but not exclusively) the down-regulation of factors including IGF-I, and signal transduction proteins such as mTOR and PKA. Advantageously, the methods of the present invention cause a reduction in a variety of amino acids, insulin and glucose while increasing ketone bodies (KB) (see FIG. 1 described below in detail). In particular, the methods induce cancer cells, which are typically in a glycolytic state (Warburg effect), to switch and rely on respiration for energy production and survival. All these molecules, actors and proteins modulate normal-cell growth in part by regulating serine/threonine protein kinases. Virtually all cancer cells have mutations in oncogenes, which make them unresponsive to external changes. However, internally the cancer cells can in some cases switch to an alternative pathway. Advantageously, this phenomenon supports the inventive concept of administrating kinases inhibitors with STS/FMD, in which the STS/FMD prevent or inhibit the activation of the alternative pathways.

Specific kinases and other growth inhibitors can reduce cancer progression, particularly if the inhibitor acts downstream of the oncogenic mutation. The multiple changes induced by STS and FMD promote an additional growth inhibitory effect that can affect pathways not targeted by the kinase inhibitor. In particular, FMD causes a significant reduction in a wide variety of nutrients along with a significant increase in others such as ketone bodies and fatty acids, Therefore, the combination of STS and FMD with kinase inhibitors provides a synergistic pro-death role with inhibitors of kinases and other proteins affecting cell growth. These effects can occur during STS/FMD regimen but can be potentiated further by chemotherapy (see FIGS. 3 and 4 described below). In addition, kinases and other signal transduction inhibitors can delay cancer growth but also cause major side effects and even death (FIG. 2D) to normal cells. The STS or FMD reverses the increased mortality induced by the co-administration of kinase inhibitors with chemotherapy, in part by reducing the activity of the pathways affected by the kinase inhibitor in normal cells (see FIG. 2 described below).

Examples of STS and FMD protocols that can be used in the present embodiments are found in U.S. patent application Ser. Nos. 12/430,058 and 13/488,590; the entire disclosures of which are hereby incorporated by reference. In a variation, the reduced caloric diet provides a hypo-caloric or calorie free diet. The diet contains dietary materials capable of providing nutrition to a human subject while providing no more than 1000 kcal per day, and in particular, no more than 813-957 kcal per day. In a variation, the reduced caloric diet provides from about 100 to 1000 kcal per day to the subject. In a refinement, the reduced caloric diet provides at most, in increasing order of preferences 1000, 957, 700, 500, 300, or 100 kcal per day to the subject. In still another refinement, the diet provides 0 kcal per day.

In variations of the embodiments set forth herein, the reduced caloric diet provides protein to the subject in an amount that is less than or equal to 30-36 g per day. In a refinement, the reduced caloric diet provides protein to the subject in an amount that is less than or equal to, in increasing order of preference, 40, 35, 20, 10, or 5 g, or 0 g per day. If carbohydrates are present in the dietary materials, no more than half of the energy of the reduced caloric diet is in the carbohydrates. In a refinement, the STS/FMD diet may be administered to the subject for 3-10 consecutive days prior to when the subject is exposed to chemotherapy. The diet may also be administered to the subject for 24 hours following the exposure. Preferably, the diet may be administered to the subject for both 3-10 consecutive days prior to when the subject is exposed to chemotherapy and 24 hours following the exposure.

In a variation of each of the embodiment set forth herein, the kinase inhibitor can be administered within a week of the start of a cycle of the reduced caloric diet (i.e., the first time period). In still another refinement, the kinase inhibitor can be administered within 1, 2, 3, 4, or 5 days of the start of a cycle the reduced caloric diet. In another variation, the kinase inhibitor is administered after but within a week of the end of a cycle of the reduced caloric diet. In still another refinement, the kinase inhibitor can be administered after but within 1, 2, 3, 4, or 5 days of the end of a cycle the reduced calorie diet. In another variation, the reduced caloric diet is administered for a total time period of 3 days to 14 days per treatment cycle. In still another refinement, the reduced caloric diet is administered for a total time period per treatment cycle of 3 days to 10 days. As set forth above, the steps of administering the reduced caloric diet, administering of the chemotherapeutic agent (when used), and administering of the kinase inhibitor constitute a treatment cycle that can be repeated a plurality of times at predetermined intervals. For example, this treatment cycle can be repeated at intervals from two weeks to two months. In a refinement, this treatment cycle can be repeated at intervals from two weeks to 1 month.

In other variations of the embodiments set forth herein, the reduced caloric diet provides nutrition while providing no more than 11 kcal (e.g., no more than 8, 5, or 2 kcal, or 0 kcal) energy per kg body weight of the subject per day and no more than 0.4 g (e.g., 0.3, 0.2, or 0.1 g or 0 g) protein per kg body weight of the animal or human per day. If carbohydrates are present in the diet, no more than half of the energy is in the carbohydrates. In some embodiments, the diet is capable of providing no more than 700 kcal (e.g., 600, 400, or 200 kcal or 0 kcal) total energy per day. When the subject is exposed to chemotherapy, normal cells, but not abnormal cells such as cancer cells, in the animal or human are protected. For example, the diet may be administered to the animal or human for 3-10 consecutive days prior to the subject's exposure to chemotherapy. The diet may also be administered to the subject for 24 hours following the exposure. Preferably, the diet may be administered to the subject for both 3-10 consecutive days prior to the subject's exposure to chemotherapy and 24 hours following the exposure.

In another variation, the STS/FMD protocol used for the reduced caloric diet involves fasting mimicking diets. For example, the subject suffering from cancer may be fasted for 48-140 hours prior to one round of chemotherapy or 4-56 hours following the chemotherapy. Preferably, the subject suffering from cancer is given a FMD for 48-140 hours prior to one round of chemotherapy and 4-56 hours following the chemotherapy.

Examples of FMD diets are found in U.S. patent application Ser. Nos. 14/060,494 and 14/178,953; the entire disclosures of which are hereby incorporated by references. Typically, in the FMD protocol a subject's diet is substituted for a predetermined number of days (i.e. 5 days). During this period, subjects consume plenty of water. For healthy subjects of normal weight (Body Mass Index or BMI between 18.5-25), the diet is consumed once a month (5 days on the diet and 25-26 days on their normal diet) for the first 3 months and every 3 months thereafter (5 days every 3 months). The weight of the subject is measured and the subject must regain at least 95% of the weight lost during the diet before the next cycle is begun. Subjects with BMI of less than 18.5 should not undertake the FMD unless recommended and supervised by a physician. The same regimen (once every month for 3 months followed by once every 3 months thereafter) can be adopted for the treatment, or in support of the treatment, of all of the conditions presented in the patent applications. U.S. patent application Ser. No. 14/178,953 provides a low protein version of the FMD diet.

As set forth above, the embodiments of the invention call for the administration of a kinase inhibitor, and in particular, an mTOR kinase inhibitor. Rapamycin is one particularly useful mTOR kinase inhibitor. Typically, rapamycin is administered in a dosage of 5 to 20 mg per day. Examples of other kinase inhibitors include, Afatinib (Gilotrif) (target is EGFR/ErbB2 for treating non-small cell lung carcinoma (NSCLC)—40 mg orally once daily); Axitinib (target is VEGFR1/VEGFR2/VEGFR3/PDGFRB/c-KIT for treating Renal Cell Carcinoma—5 mg twice daily); Ruxolitinib (target is JAK for treating myelofibrosis—between 5 and 25 mg orally twice a day depending on the WBC count); Imatinib (gleevec) (target is Bcr—Abl for treating chronic myelogenous leukemia (CML)—400 mg to 600 mg once daily); Vemurafenib (Zelboraf) (target is BRAF for treating late stage melanoma—960 mg every 12 hours); Bosutinib (Bosulif) (target is BcrAbl/SRC for treating Chronic Myelogenous Leukemia—500 mg once a day with food); and combinations thereof.

An FMD for mammal subjects and in particular humans, substitutes the normal diet of a cancer patient for a period of 5 to 21 days with a 17 day maximum for most patients (see below) with frequency to be determined based on the frequency and efficacy of other treatments, with more frequent use needed when other treatments are not effective in cancer treatment. The ability of the patient to regain weight before the next cycle is initiated must also be considered, with patients with more severe symptoms able to regain weight receiving the diet as frequently as the other treatments are given and patients who are not regaining weight or are unable to undergo the full dietary period being placed on the FMD only after they return to the normal weight (weight before treatment is initiated but also BMI above 18). The FMD consists of ingredients which are Generally Regarded As Safe (RGAS). Calories are consumed according to the subject's body weight. For day 1, total calorie consumption is 4.5-7 kilocalories per pound (or 10-16 kilocalories per kilogram). The diet should be at least 90% plant based. The day 1 diet should contain less than 30 g of sugars, less than 28 g of plant based proteins, 20-30 grams of plant based monounsaturated fats, 6-10 g of plant based polyunsaturated fats and 2-12 g of plant based saturated fats. For days 2-21, total calorie consumption is 3-5 kilocalories per pound (or 7-11 kilocalories per kilogram). The days 2-21 diet should contain less than 20 g of sugars, less than 18 g of plant based proteins, 10-15 g of plant based monounsaturated fats, 3-5 g of plant based polyunsaturated fats and 1-6 grams of plant based saturated fats, 10-30 grams of glycerol diluted in 1 liter of water/day, based on body weight (10 grams for a 100 pound person, 20 grams for a 200 pound person and 30 grams for a 300 pound person). Diet should also be high nourishment containing approximately 50% of the RDA (daily) for vitamins, minerals+essential fatty acids. The minimum length will be 5 or 6 days and the maximum length 21 days (based on safety data and standard of care practice at fasting clinics).

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

DSS and DSR Experiments

The methods of the present invention have been largely tested in in vitro and in vivo murine models. STS and FMD have also been tested in different clinical trials, which have shown the safety and feasibility of the two dietary interventions. FMD diet has shown to be as effective as STS in evoking both DSS and DSR.

Figure 1B:
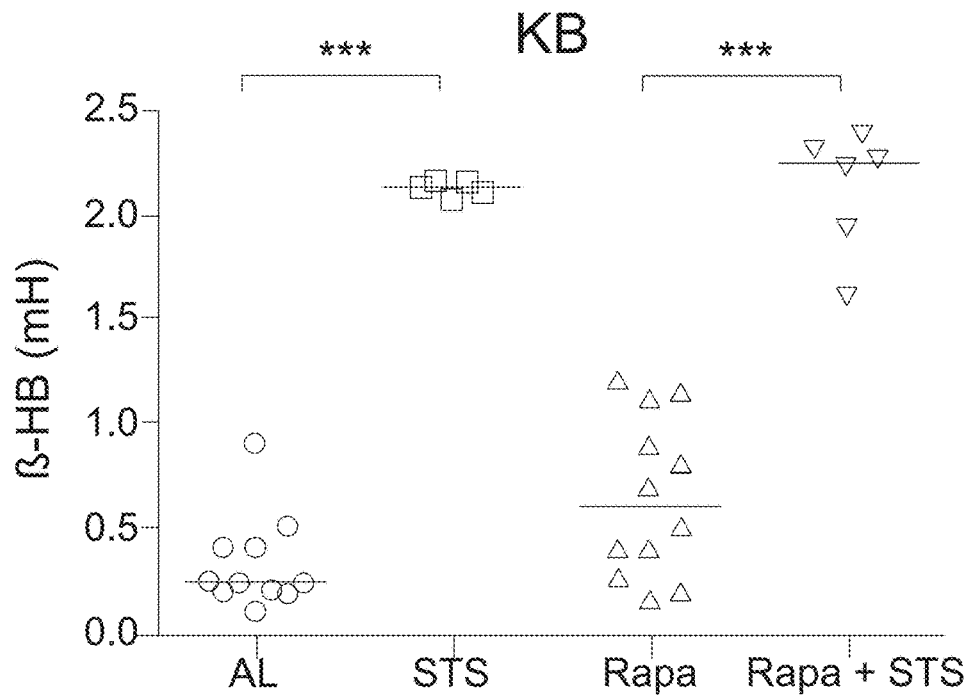
FIG. 1B provides plots of ketone body levels for mice treated STS, Rapamycin, and rapamycin with STS.

Methods: Short term starvation (STS) or fasting mimicking diet (FMD) were administrated bi-weekly for periods of 48 h or 4 days, respectively. The end of the dietary intervention coincided with the administration of doxorubicin by intravenous injection. The animals were given a period of 10 to 12 days to recover bodyweight between one cycle of dietary intervention and the next. Rapamycin was administrated intraperitoneally every day during the ad lib feeding but not during dietary intervention, for the entire duration of the experiment. Physiological and molecular markers such as circulating glucose, ketone bodies and S6K levels were observed in order to validate the efficacy of the treatment. FIG. 1A shows that rapamycin treatment induces an insulin-resistance-like state causing an increase of blood glucose. The decreased blood glucose in Rapa+STS/FMD mice supports the hypothesis that mice treated with Rapa and STS/FMD are more resistant than mice treated with rapamycin alone. FIG. 1B shows that as expected, ketone bodies (KB) levels were significantly increased during STS/FMD, with or without rapamycin administration. One-way ANOVA test was performed and differences with p-value<0.05 were considered significant (p-value<0.05, 0.01 and 0.001 are indicated as *, *, and ***, respectively).

Diet (mouse): Mice were maintained on irradiated TD.7912 rodent chow (Harlan Teklad). In brief, this diet contains 3.T5 kcal/g of digestible energy with calories supplied by protein, carbohydrate and fat in a percent ratio of 25:58:17. Food was provided ad lib. On average, mice in the control group consumed 14.9 kcal/day (or 3.9 g/day), Our experimental FMD diet is based on a nutritional screen that identified ingredients allowing high nourishment during periods of low calorie consumption (Brandhorst, Wei et al., 2013. Exp Gerontol. 2013 October; 48(10):1120-8. doi: 10.1016/j.exger.2013.02.016. Epub 2013 Feb. 21). Prior to supplying the FMD diet, animals were transferred into fresh cages to avoid feeding on residual chow and coprophagy. The FMD diet consists of two different components designated as day 1 diet and day 2-4 diet that were fed in this order, respectively. The day 1 diet contains 1.88 kcal/g and was designed to adapt the mouse to a period of low caloric intake during the subsequent feeding days. The day 2-4 diet is identical on all feeding days and contains 0.36 kcal/g. The day 1 and days 2-4 diets were fed as the average intake (~4 g) of the ad lib fed control group every two weeks. Due to the different caloric densities of the supplied FMD diet, mice in this cohort had a ~50% reduction in consumed calories on day 1 and consumed 9.7% of the control cohort on days 2 to 4. Mice consumed all the supplied food on each day of the FMD regimen and showed no signs of food aversion. After the end of the day 2-4 diet, we supplied TD.7912 chow ad lib for 10 days before starting another FMD cycle.

Figure 2A:
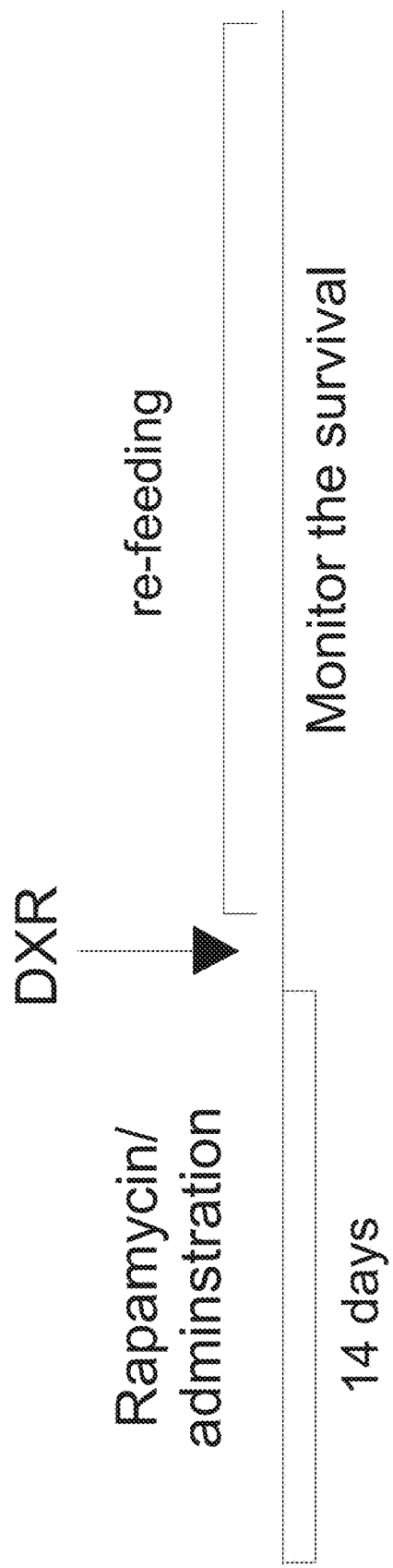
FIG. 2A provides a schematic timeline indicating the schedule for the stress resistance experiment administered to 12 week old female C57BL/6 mice.
Figure 2B:
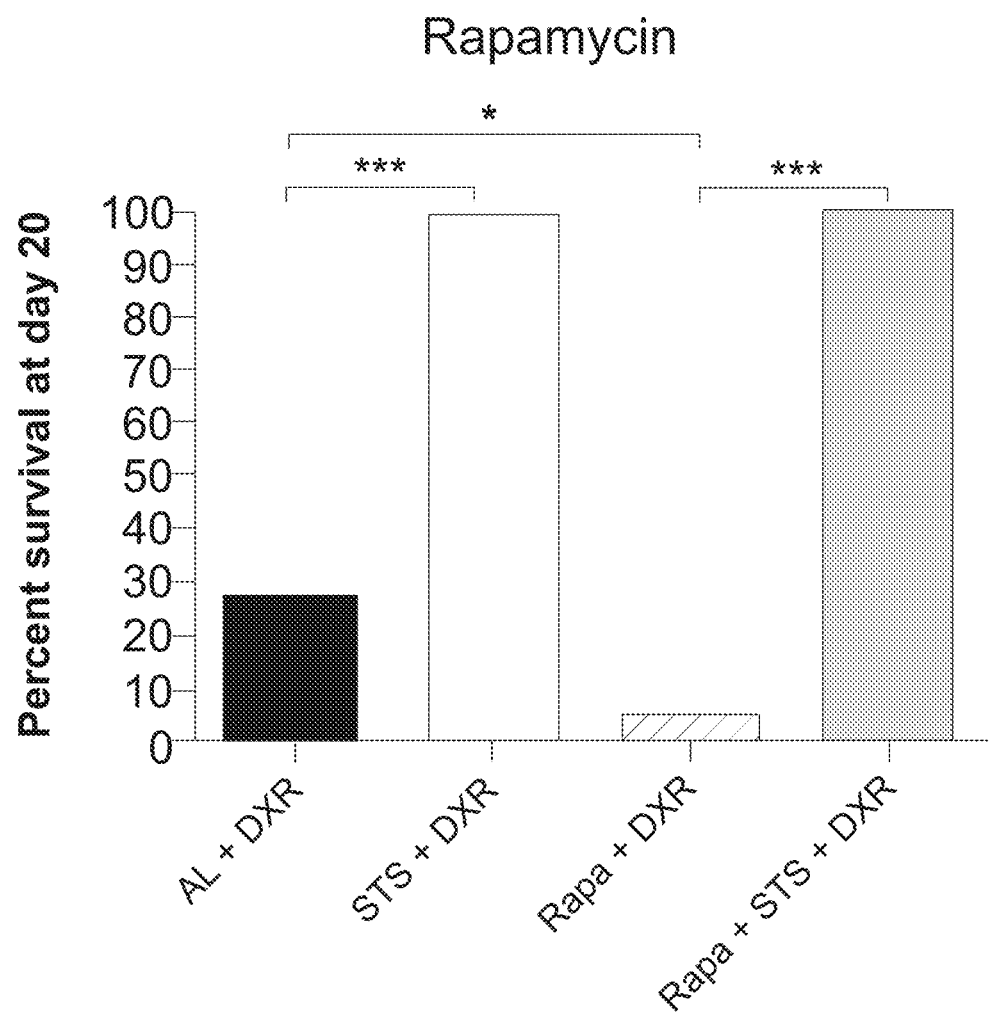
FIG. 2B provides survival results at day 20 (end-time point) for the experiment of FIG. 3A.
Figure 2C:
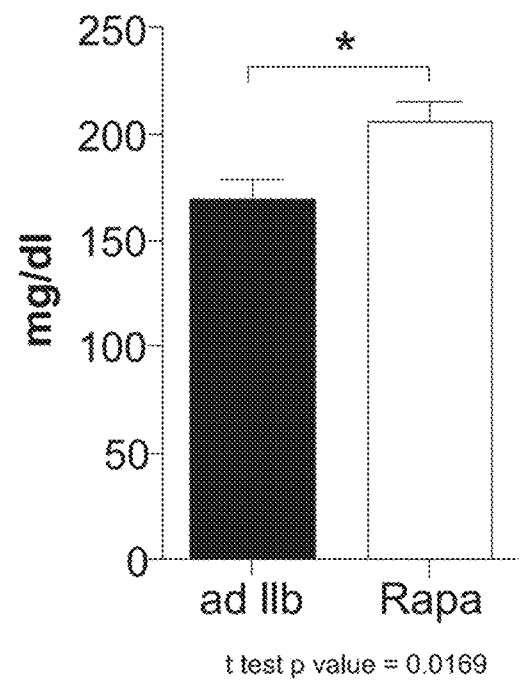
FIG. 2C provides a plot of blood glucose levels to confirm the effectiveness of STS for FIG. 3A.

FIGS. 2A-C provide experimental results showing induced stress resistance in mice. In these experiments, 12 week old female C57BL/6 mice were divided in the following experimental groups; ad lib (ad libitum feeding), STS/FMD, DXR, STS/FMD+DXR (FIG. 2). In order to observe the response to every treatment in presence or not of rapamycin, each group was present as duplicate but only one underwent rapamycin treatment. The administration of rapamycin was performed for a period of 14 days at the end of which a high dose of doxorubicin was administrated iv (24 mg/kg/). The animals belonging to the STS+DXR groups were fed a very low calorie and no protein FMD for 48 h prior the injection of doxorubicin. Following doxorubicin injection the animal were monitored every day and the survival was recorded (FIG. 2). FIG. 2A provides the treatment schedule for this stress resistance experiment. FIG. 2B provides the survival data at day 20. FIG. 2C provides a plot of the blood glucose levels for each of the experimental groups. It is also observed that the administration of rapamycin during chemotherapy sensitizes the mice to the drug leading to an increased mortality. However the experiment of FIG. 2B show that STS can reverse the sensitization of normal tissue to chemotherapy induced by rapamycin.

Cancer Related Experiments

A mTOR kinase inhibitor rapamycin in combination with STS and with the chemotherapy drugs was administered to an animal, human subject or cancer cells to retard cancer growth and improve the survival. The chemotherapy drugs tested were the anthracycline doxorubicin alone or in a mix with two other chemo-drugs, topotecan and vincristine (TVD), which are commonly used to treat adult and children with cancer.

Figure 3A:
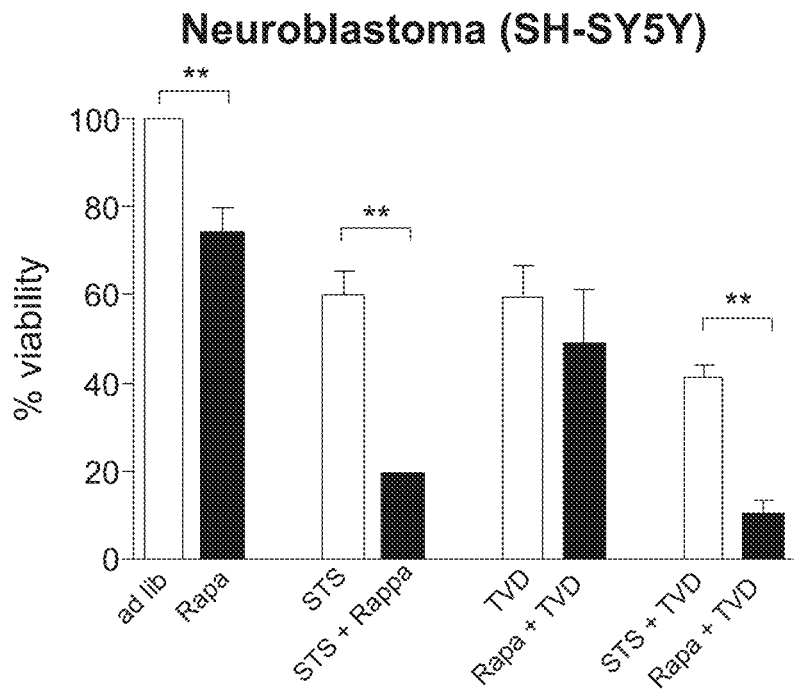
FIG. 3A provides plots of the cell viability for human neuroblastoma cell lines treated with rapamycin and the chemotherapy-drug cocktail TVD (topotecan+vincristine+doxorubicin) under ad lib feeding or STS conditions.
Figure 3B:
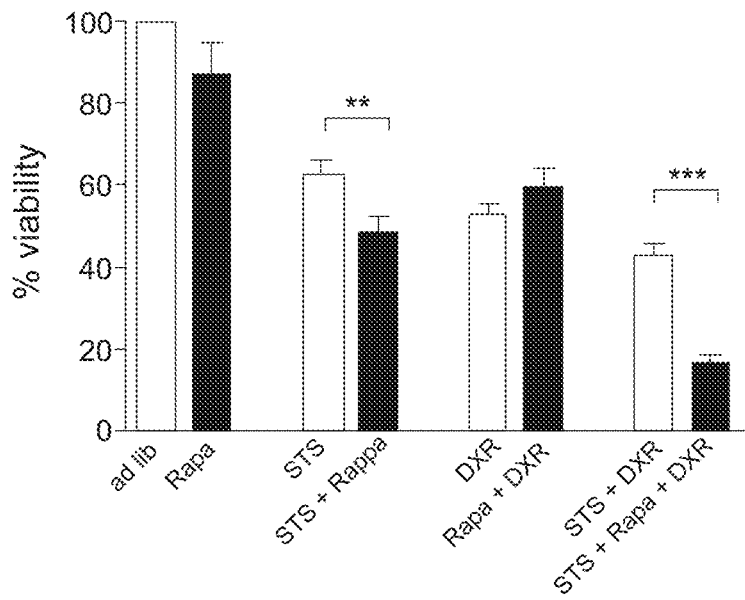
FIG. 3B provides plots of the cell viability for murine breast cancer (4T1) cell line treated with rapamycin and the chemotherapy drug doxorubicin (DXR) under ad lib feeding or STS conditions.
Figure 3C:
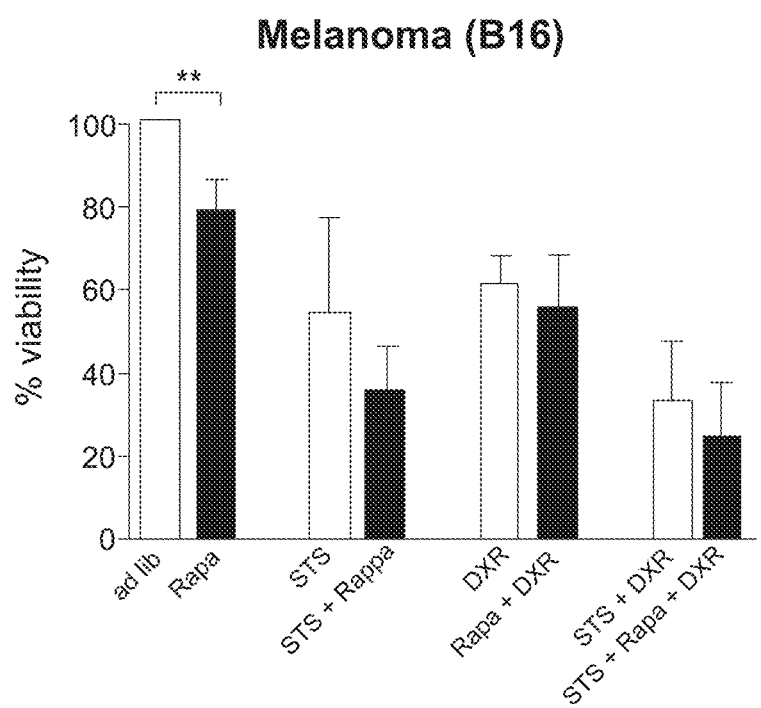
FIG. 3C provides plots of the cell viability for murine melanoma (B16) cell line treated with rapamycin and the chemotherapy drug doxorubicin (DXR) under ad lib feeding or STS conditions.

FIGS. 3A-B provide results for experiments in which the efficacy of STS in combination with rapamycin in reducing tumor growth were tested in vitro on human neuroblastoma (SH-SY5Y), murine breast cancer (4T1) and murine melanoma (B16) cell lines. FIG. 3A provides plots of the cell viability for human neuroblastoma cell lines treated with rapamycin and the chemotherapy drug cocktail TVD (topotecan+vincristine+doxorubicin) under ad lib feeding or STS conditions. FIG. 3B provides plots of the cell viability for a breast cancer (4T1) cell line treated with rapamycin and the chemotherapy drug doxorubicin (DXR) under ad lib feeding or STS conditions. FIG. 3B provides plots of the cell viability for a melanoma (B16) cell line treated with rapamycin and the chemotherapy drug doxorubicin (DXR) under ad lib feeding or STS conditions. In each of these experiments, the cell viability was determined by Trypan blue staining for all the cell line tested and the effectiveness of each treatment on viability was determined by performing Student t-test (p-value<0.05, 0.01 and 0.001 are indicated as *, *, and ***, respectively). The results show that short term starvation (STS) augments the efficacy of rapamycin and chemotherapy in reducing cell viability in multiple cancer cell lines.

Figure 4A:
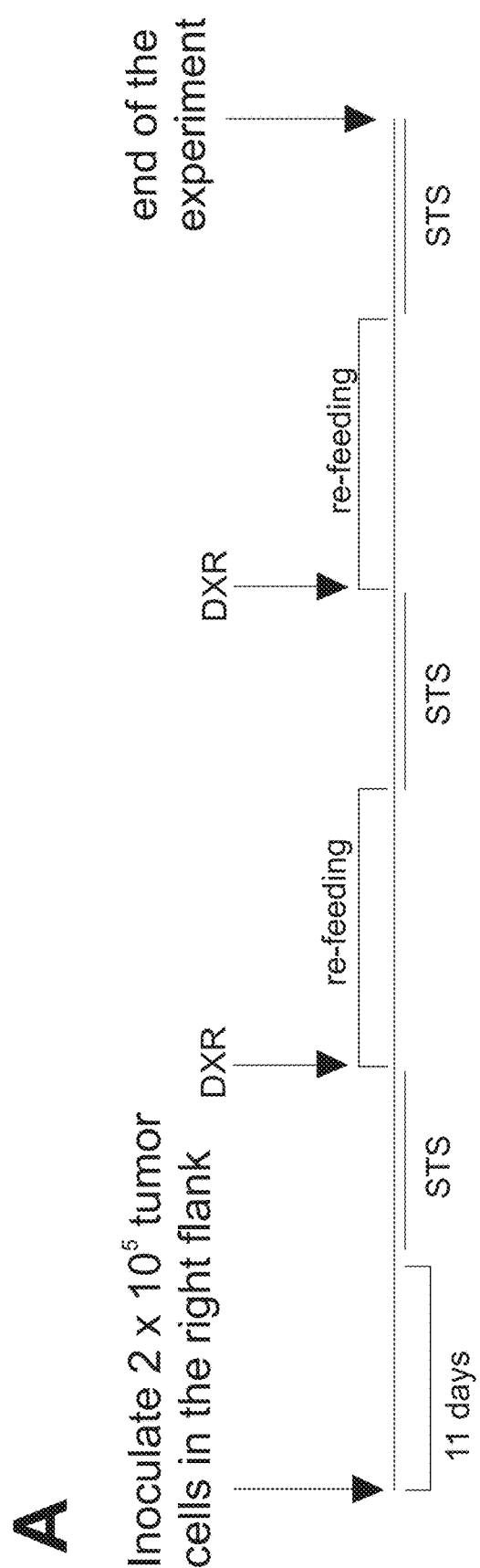
FIG. 4A provides the timeline indicating the schedule for the tumor progression studies involving a reduced caloric diet and rapamycin.
Figure 4B:
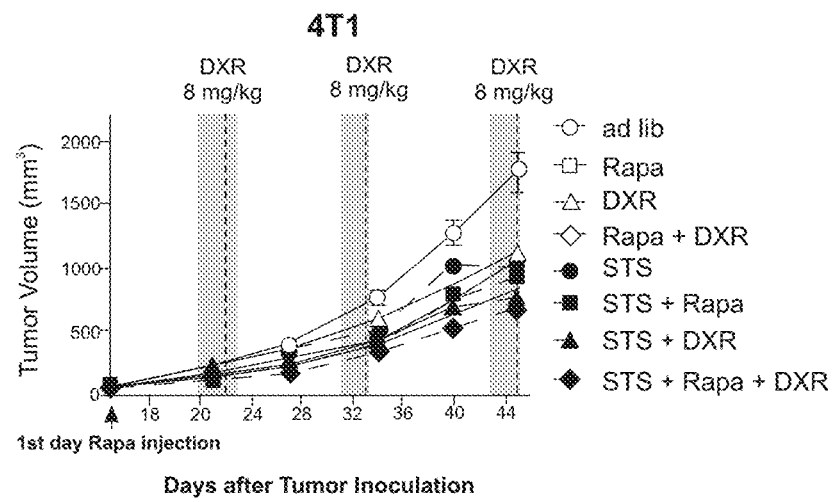
FIG. 4B provides a plot of the tumor volume versus time for a 4T1 murine breast cancer model in BALB/c mice treated with rapamycin and multiple cycles of STS combined with DXR administration.
Figure 4C:
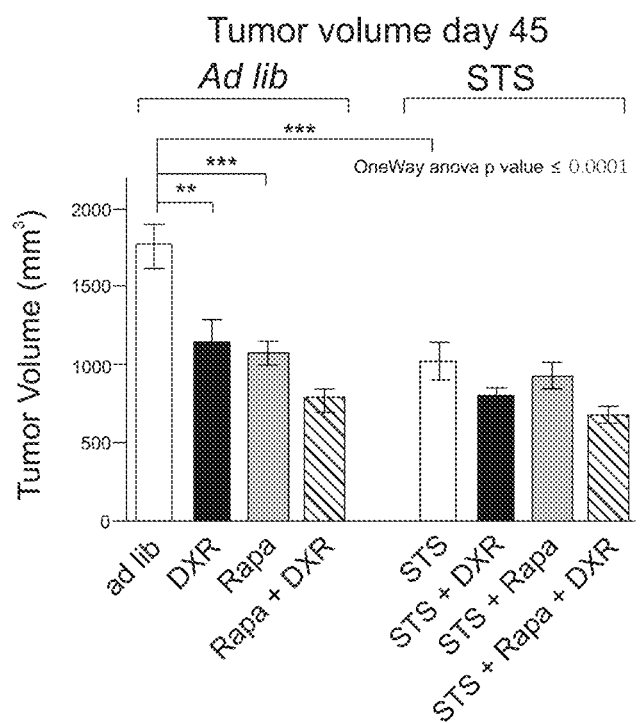
FIG. 4C is a bar chart indicating tumor volume at the end of the experiment in FIG. 4B.
Figure 4D:
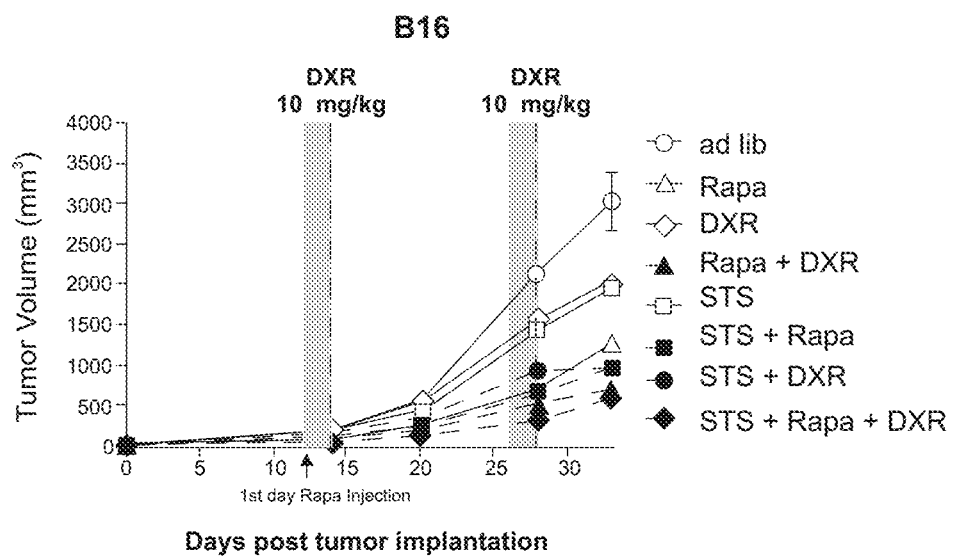
FIG. 4D provides a plot of the tumor volume versus time for a murine melanoma model in C57BL/6 mice treated with rapamycin and multiple cycles of STS combined with DXR administration.
Figure 4E:
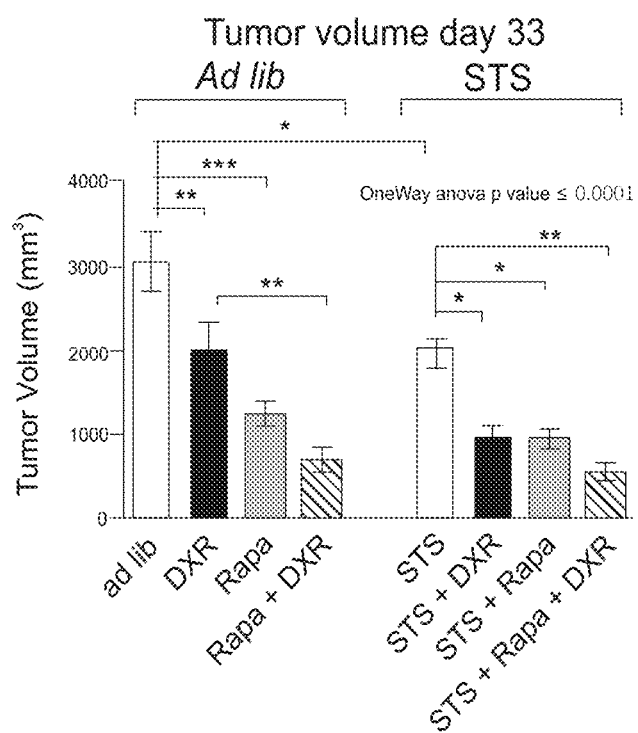
FIG. 4E is a bar chart indicating tumor volume at the end of the experiment in FIG. 4D.

In a murine breast cancer (4T1) and murine melanoma (B16) mouse allograft models, it is demonstrated that STS and rapamycin have an additive effect in reducing tumor progression, which confirms that STS potentiates the effects of the mTOR kinase inhibitor rapamycin on cancer cells. FIGS. 4A-E provide the results of tumor progression studies. FIG. 4A provides the timeline for the indicating the schedule indicating the schedule for the tumor progression studies involving a reduced caloric diet and rapamycin. In general, Balb/c and C57BL/6 mice were injected subcutaneously with $2\times10^5$ 4T1 or B16 cells respectively. Once the tumor was palpable, the mice were grouped and underwent multiple cycles of STS combined with DXR administration. FIG. 4B provides a plot of the tumor volume versus time for a 4T1 murine breast cancer model in Balb/c mice treated rapamycin and multiple cycles of STS (Shaded bar in A) combined with DXR administration. FIG. 4C is a bar chart indicating tumor volume at the end of the experiment in FIG. 4B. FIG. 4D provides a plot of the tumor volume versus time for a murine melanoma model in C57BL/6 mice treated rapamycin and multiple cycles of STS combined with DXR administration. FIG. 4E is a bar chart indicating tumor volume at the end of the experiment in FIG. 4D. One-way ANOVA analysis was performed to determine the significance of the tumor size differences and the effectiveness of the treatment tested (p-value<0.05, 0.01 and 0.001 are indicated as *, *, and ***, respectively). For the 4T1 murine breast cancer model, female Balb/c mice were injected subcutaneously s.c. in the right flank with $2\times10^5$ 4T1 cancer cells and ad lib fed with standard diet until the tumor was palpable. For our B16 murine melanoma model, female C57BL/6 mice were injected subcutaneously s.c. in the right flank with $2\times10^5$ B16 cancer cells and ad lib fed with standard diet until the tumor was palpable. At this point the tumor volume was determined and the mice were arranged in the following experimental groups; ad lib (ad libitum feeding), STS/FMD, DXR, STS/FMD+DXR. In order to observe the response to every treatment in presence or not of rapamycin, each group was present as duplicate but only one underwent rapamycin treatment. The mice were subject to a daily injection of rapamycin and to a multi-cycle treatment (for a total of three) where each cycle was composed as follows: mice belonging to the STS/FMD and STS/FMD+ DXR groups underwent 48 to 72 h of complete food deprivation with free access to water and then re-fed with standard chow diet for ~10 days between cycles to recover the bodyweight lost. The animals from the STS/FMD+DXR group were also injected intravenously with Doxorubicin at the end of the first, second and third cycle respectively. The animals from DXR group were ad lib fed and injected with Doxorubicin as well. The experiments show that fasting enhances the effect of rapamycin in decreasing tumor progression.

In summary, the combination of STS/FMD with the mTOR inhibitor rapamycin has additive effects in retarding the growth and survival of a wide variety of cancer cells and tumors. This combined treatment also prevents the chemotherapy-dependent sensitization of normal cells caused by the administration of rapamycin alone. The results suggest that STS/FMD can potentiate the effect of other inhibitors of nutrient signaling pathways including the AKT-TOR-S6K and Ras-cAMP-PKA and MAPK. Because of the wide/ broad acting effect of STS or the equivalent FMD on a variety of molecules, growth factors and nutrients outside and inside of cells, the potentiating effect observed with rapamycin is expected to apply to many different kinase/ growth inhibitors used in cancer treatment. Because rapamycin and many other kinase and/or growth inhibitors are widely used for the treatment of certain tumors in humans, these results have important implications for the safety and efficacy of those therapies.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for treating cancer, the method comprising:
    a) identifying a subject having cancer;
    b) administering a reduced caloric diet to the subject for a first time period, the reduced caloric diet providing at most 957 kcal per day, the reduced caloric diet providing:
    on a first day less than 30 g of sugars, less than 28 g of plant based proteins, 20-30 grams of plant based monounsaturated fats, 6-10 g of plant based polyunsaturated fats and 2-12 g of plant based saturated fats; and
    on days 2 to a final diet day less than 20 g of sugars, less than 18 g of plant based proteins, 10-15 g of plant based monounsaturated fats, 3-5 g of plant based polyunsaturated fats and 1-6 grams of plant based saturated fats, 10-30 grams of glycerol diluted in 1 liter of water/day, the reduced caloric diet being administered for a minimum length of 6 days and a maximum length of 21 days, the reduced caloric diet providing less than 20 g of protein per days; and c) administering a kinase inhibitor to the subject to reduce tumor progression.

2. The method of claim 1 wherein steps b) and c) are repeated a plurality of times at predetermined intervals.

3. The method of claim 2 wherein steps b) and c) are repeated at intervals from two weeks to 2 months.

4. The method of claim 2 wherein the subject is administered a normal diet in between repetition of steps b) and c).

5. The method of claim 1 wherein the kinase inhibitor is administered during the first time period.

6. The method of claim 1 wherein the kinase inhibitor is administered after but within a week of the first time period.

7. The method of claim 1 further comprising administering a chemotherapeutic agent to the subject after the first time period.

8. The method of claim 7 wherein the reduced caloric diet is administered to the subject for a second time period after treatment with the chemotherapeutic agent commences.

9. The method of claim 7 wherein the chemotherapeutic agent is selected from the group consisting of topotecan, vincristine, doxorubicin, and combinations thereof.

10. The method of claim 8 wherein the second time period is from 1 to 3 days.

11. The method of claim 1 wherein the reduced caloric diet provides at most 500 kilocalories per day.

12. The method of claim 1 wherein carbohydrates provide less than half of the calories from the reduced caloric diet.

13. The method of claim 1 wherein the subject has melanoma or neuroblastoma or breast cancer.

14. The method of claim 1 wherein the kinase inhibitor is an mTOR protein kinase.

15. The method of claim 1 wherein a chance of survival for the subject is increased.

16. The method of claim 1 wherein the reduced caloric diet provides less than 5 g of protein per day.

17. The method of claim 1 wherein the reduced caloric diet provides at most 700 kcal per day.

18. A method for treating cancer and/or alleviating a symptom of chemotherapy, the method comprising:

a) identifying a subject having cancer;

b) administering a reduced caloric diet to the subject for a first time period, the reduced caloric diet providing at most 957 kcal per day, the reduced caloric diet providing:

on a first day less than 30 g of sugars, less than 28 g of plant based proteins, 20-30 grams of plant based monounsaturated fats, 6-10 g of plant based polyunsaturated fats and 2-12 g of plant based saturated fats; and on days 2 to a final diet day less than 20 g of sugars, less than 18 g of plant based proteins, 10-15 g of plant based monounsaturated fats, 3-5 g of plant based polyunsaturated fats and 1-6 grams of plant based saturated fats, 10-30 grams of glycerol diluted in 1 liter of water/day, the reduced caloric diet being administered for a minimum length of 6 days and a maximum length of 21 days, the reduced caloric diet providing less than 20 g of protein per day;

c) administering a chemotherapeutic agent to the subject after the first time period; and d) administering a kinase inhibitor to the subject, wherein the chemotherapeutic agent is different than the kinase inhibitor.

19. The method of claim 18 wherein steps b) and c) are repeated a plurality of times at predetermined intervals.

20. The method of claim 19 wherein steps b) and c) are repeated at intervals from two weeks to 2 months.

21. The method of claim 20 wherein the subject is administered a normal diet in between repetition of steps b) and c).

22. The method of claim 18 further comprising administering the reduced caloric diet to the subject for a second period of time after administering of the chemotherapeutic agent.

23. A method for alleviating a side effect of kinase inhibitor treatment, the method comprising:

a) identifying a subject being treated with a kinase inhibitor;

b) administering a kinase inhibitor to the subject; and c) administering a reduced caloric diet to the subject for a first time period that is after the step of administering a kinase inhibitor, the reduced caloric diet providing at most 957 kcal per day and alleviating a side effect of kinase inhibitor treatment wherein the reduced caloric diet provides;

on a first day less than 30 g of sugars, less than 28 g of plant based proteins, 20-30 grams of plant based monounsaturated fats, 6-10 g of plat based polyunsaturated fats and 2-12 g of plant based saturated fats; and on days 2 to a final diet day less than 20 g of sugars, less than 18 g of plant based proteins, 10-15 g of plant based monounsaturated fats, 3-5 g of plant based polyunsaturated fats and 1-6 grams of plant based saturated fats, 10-30 grams of glycerol diluted in 1 liter of water/day, the reduced caloric diet being administered for a minimum length of 6 days and a maximum length of 21 days.

* * * * *